United States Patent [19]

Brown

[11] Patent Number: 5,393,669
[45] Date of Patent: Feb. 28, 1995

[54] COMPOSITIONS AND METHODS FOR PROTEIN STRUCTURAL DETERMINATIONS

[75] Inventor: Jonathan M. Brown, Baltimore, Md.

[73] Assignee: Martek Biosciences Corp., Columbia, Md.

[21] Appl. No.: 14,243

[22] Filed: Feb. 5, 1993

[51] Int. Cl.$^6$ .......................... C12Q 1/04; C12N 5/00; G01N 33/00
[52] U.S. Cl. .................................. 435/240.3; 435/34; 435/35; 435/240.2; 435/240.31; 436/86; 436/89
[58] Field of Search ....................... 436/86, 89; 435/34, 435/35, 253.6, 240.2, 240.3, 240.31

[56] References Cited

PUBLICATIONS

S. J. Archer et al., *Biochemistry 32* (1993), pp. 1152–1163.
S. J. Archer et al., *Biochemistry 32* (1993), pp. 1164–1171.
D. M. LeMaster et al., *Analytical Biochemistry 122* (1982), pp. 238–247.
L. E. Kay et al., *Science 249* (1990), pp. 411–414.
P. C. Driscoll et al., *Nature 353* (1991), pp. 762–765.
K. Appelt et al., *Journ of Med. Chem 34* (1991), pp. 1925–1934.
V. L. Hsu et al., *Biochemistry 31* (1992), pp. 12778–12784.
A. P. Hansen et al., *Biochemistry 31* (1992), pp. 12713–12718.
G. J. Cox, *J. Biol. Chem. 78* (1928), pp. 475–479.
J. D. Watson et al., *Nature 171* (1953), pp. 737–738.
M. F. Perutz, *Nature 185* (1960) pp. 416–422.

*Primary Examiner*—Herbert J. Lilling
*Attorney, Agent, or Firm*—Rothwell, Figg, Ernst & Kurz

[57] ABSTRACT

A method for determining three-dimensional structural information of a protein involves producing the protein in a form substantially labeled with $^{13}C$ or $^{15}N$ or both and subjecting the protein to nuclear magnetic resonance spectroscopic analysis. The isotopically labeled protein is produced by a method which involves producing a substantially labeled microbial protein hydrolysate, subjecting the protein hydrolyzate to cation exchange chromatography to produce a partially purified labeled amino acid mixture, subjecting the partially purified labeled amino acid mixture to anion exchange chromatography to produce a purified labeled amino acid mixture and supplementing the purified labeled amino acid mixture with isotopically labeled cysteine.

2 Claims, No Drawings

COMPOSITIONS AND METHODS FOR PROTEIN STRUCTURAL DETERMINATIONS

FIELD OF THE INVENTION

This invention is concerned with the determination of the three-dimensional structure of biological macromolecules, especially proteins. In particular, it is concerned with novel compositions and methods for the determination, by NMR spectroscopy, of the three-dimensional structure of proteins expressed in cultures of mammalian or insect cells.

BACKGROUND OF THE INVENTION

For many years, there has been intense interest in the determination of the three-dimensional structure of biological macromolecules, particularly proteins. So-called "structure-function" studies have been carried out with a view to determining which structural features of a molecule, or class of molecules, are important for biological activity. Since the pioneering work of Nobel laureates, Perutz and coworkers on the structure of hemoglobin (Perutz, M. F. et al., *Nature*, 185, 416–422 (1960)) and Watson and Crick on the structure of DNA (Watson, J. D. and Crick, F. H. C., *Nature*, 171, 737 (1953)), this field has been of major importance in the biological sciences.

More recently, there has evolved the concept of "rational drug design." This strategy for the design of drugs involves the determination of the three-dimensional structure of an "active part" of a particular biological molecule, such as a protein. The biological molecule may, for example, be a receptor, an enzyme, a hormone, or other biologically active molecule. Knowing the three-dimensional structure of the active site can enable scientists to design molecules that will block, mimic or enhance the natural biological activity of the molecule. (Appelt, K., et al., *J. Med. Chem.*, 34, 1925 (1991)). The determination of the three-dimensional structure of biological molecules is therefore also of great practical and commercial significance.

The first technique developed to determine three-dimensional structures was X-ray crystallography. The structures of hemoglobin and DNA were both determined using this technique. X-ray crystallography involves bombarding a crystal of the material to be examined with a beam of X-rays which are refracted by the atoms of the ordered molecules in the crystal. The scattered X-rays are captured on a photographic plate, which is then developed using standard techniques. The diffracted X-rays are thus visualized as a series of spots on the plate, and from this pattern, the structure of the molecules in the crystal can be determined. For larger molecules, it is also necessary to crystallize the material with a heavy ion, such as ruthenium, in order to remove ambiguity due to phase differences.

More recently, another technique, nuclear magnetic resonance ("NMR") spectroscopy, has been developed to determine the three-dimensional structures of biological molecules, and particularly proteins. NMR spectroscopy was originally developed in the 1950's and has evolved into a powerful procedure for analyzing the structure of small compounds, such as those with a molecular weight of $\leq 1000$ daltons. Briefly, the technique involves placing the material (usually in a suitable solvent) in a powerful magnetic field and irradiating it with a strong radio signal. The nuclei of the various atoms will align themselves with the magnetic field until energized by the radio signal. They then absorb this energy and re-radiate (resonate) it at a frequency dependent on i) the type of nucleus and ii) the chemical environment (determined largely by bonding) of the nucleus. Moreover, resonances can be transmitted from one nucleus to another, either through bonds or through three dimensional space, thus giving information about the environment of a particular nucleus and nuclei in the vicinity of it.

However, it is important to recognize that not all nuclei are NMR active. Indeed, not all isotopes of the same element are active. For example, whereas "ordinary" hydrogen, $^1H$, is NMR active, heavy hydrogen (deuterium), $^2H$, is not. Thus, any material that normally contains $^1H$ hydrogen can be rendered "invisible" in the hydrogen NMR spectrum by replacing all the $^1H$ hydrogens with $^2H$. It is for this reason that NMR spectra of water-soluble materials are determined in solution in $^2H_2O$, so as to avoid the water signal.

Conversely, "ordinary" carbon, $^{12}C$ is NMR inactive whereas the stable isotope $^{13}C$, present to about 1% of total carbon in nature, is active. Similarly, "ordinary" nitrogen, $^{14}N$, is NMR inactive whereas the stable isotope $^{15}N$, again present to about 1% of total nitrogen in nature, is active. For small molecules, it was found that these low level natural abundancies were sufficient to generate the required experimental information, provided that the experiment was conducted with sufficient quantities of materials and for sufficient time.

As advances in hardware and software were made, the size of molecules that could be analyzed by these techniques increased to about 10,000 Daltons, the size of a small protein. The application of NMR spectroscopy to protein structural determinations therefore began only a few years ago. It was quickly realized that this size limit could be raised by substituting the NMR active stable isotopes $^{15}N$ and $^{13}C$ into the proteins in place of the NMR inactive isotopes $^{14}N$ and $^{12}C$. A method of achieving this substitution was to grow microorganisms capable of producing the proteins in growth media labeled with these isotopes.

Over the past two or three years, $^{15}N$-labeling and $^{13}C$-labeling of proteins, have raised the analytical size limit to approximately 15 kd and 30 kD (40 kD projected) respectively. This isotopic substitution has been accomplished by growing a bacterium or yeast, transformed by genetic engineering to produce the protein of choice, in a growth medium containing and/or $^{15}N$ labeled substrates. In practice, these media usually consist of $^{13}C$ labeled glucose and/or $^{15}N$ labeled ammonium salts. (Kay, L. et al., *Science*, 249, 411 (1990) and references therein.) Recently, bacterial and yeast nutrient media containing labeled protein hydrolyzates have been described. See International Patent Application, publication no. WO 90/15525, published Dec. 27, 1990.

Heretofore, compositions and methods for NMR structural determinations have suffered from a significant limitation. Most proteins of interest in structure-function studies are mammalian in origin. Moreover, virtually all proteins of interest in rational human drug design are mammalian, i.e., human, in origin. Yet neither X-ray crystallography nor NMR spectroscopy have had widespread use in examining proteins produced from mammalian cells. X-ray crystallography, by definition, requires crystalline material, yet mammalian cell proteins are notoriously difficult to crystallize. To date, only a few antibodies and mammalian cell-derived receptors have been crystallized in a form suitable for crystallography. Those that have been crystallized have usually been selected fragments of a molecule. Information derived from molecular fragments is viewed with caution, as it is never known whether the structure of the part of the main molecule on its own is the same as that of that part of the molecule in the whole molecule. Moreover, X-ray crystallography is inapplicable in those frequent instances in which crystalline material cannot be obtained.

NMR structural studies have hitherto been limited by the necessity of expressing the labeled proteins in bacteria or yeast. However, most mammalian proteins contain significant post-translational modifications that cannot be effected in bacterial and yeast systems. That is to say, they are appropriately folded and cross-linked with disulfide bridges, may have attached side chains of oligosaccharides and may be proteolytically cleaved to active forms. Bacterial or yeast-produced proteins frequently do not possess the biological activity of mammalian cell-produced proteins. Indeed, in some cases, mammalian proteins cannot be produced in bacteria at all. For these reasons, the biotechnology industry moved from bacterial expression systems to mammalian ones in the mid 1980's to produce recombinant therapeutic proteins, such as tissue plasminogen activator, Factor VIII:C, erythropoietin and the like. Parts of some mammalian cell proteins have been studied by NMR by cloning the gene for a fragment of the molecule of interest into a bacterium, and expressing the fragment in isotopically labeled form by growth of the bacterium in an isotopically labeled medium. Again, only those parts of a molecule of choice that can be expressed in bacteria have been susceptible to study in these systems (e.g. see Driscoll, P. C., et al., Nature, 353, Oct. 24, 1991). Because of the lack of post-translational modifications inherent in bacterial expression, the molecular parts examined have been produced in the absence of such post-translational modifications such as glycosylation etc., again leading to doubt as to the value of the structures obtained. As with X-ray crystallography, there have also been subsequent doubts as to the value of structural information obtained from protein fragments.

Host-vector systems utilizing both mammalian cells and insect cells have been developed. Mammalian cell lines, such as Chinese hamster ovary (CHO) cells, COS cells and insect-cell lines, such as the *Spodoptera frugiperda* cell lines SF9 and SF21 (Luckow, V. A. and Summers, M. D., Biotechnology, 6 47–55 (1988)), have been found to produce recombinant mammalian proteins with post-translational modifications similar to those of the natural protein.

NMR studies on mammalian and insect cell-produced proteins have been of limited value, as no means of universally incorporating stable isotopes such as $^{13}C$ or both $^{13}C$ and $^{15}N$ in an analogous manner to that for bacteria have been available. Whereas bacteria can grow on a simple mixture of glucose and salts, mammalian and insect cells require, in addition to glucose, all of the amino acids essential for growth. For instance, for the successful production of a universally $^{13}C$ and/or $^{15}N$ labeled protein from mammalian cells all of these amino acids would have to be present and all would have to be universally labeled with $^{13}C$ and/or $^{15}N$.

One theoretical way of producing an isotopically labeled medium would be to use a simple hydrolysate of an isotopically labeled protein. Unfortunately, hydrolysis of proteins to the constituent amino acids also leads to the concomitant formation of side products that are toxic to mammalian cells. Use of unpurified hydrolysates has been found to lead to rapid death of the cells. Moreover, conventional hydrolysis procedures destroy certain essential amino acids, and available means for preventing such destruction often result in toxic effects. On the other hand, techniques for the isolation and purification of individual amino acids are known. For example, LeMaster and coworkers published (Anal. Biochem., 122, 238 (1982)) a paper describing the purification of $^2H$ and $^{15}N$ amino acids. No fewer than five column chromatographic steps were required, and even then these workers were unable to isolate fully labeled cysteine and glutamine, while yields of tryptophan were "erratic." All three of these amino acids are essential for the growth of most mammalian and insect cell lines used as host cells for production of recombinant proteins. Moreover, the procedure utilized piperidine as a prime eluant of the amino acids from the preparative chromatography columns. Piperidine has been reported to be a highly toxic, controlled substance.

The procedures for the purification of the individual amino acids are thus complicated, time-consuming and low-yield and hence are uneconomical. Consequently, while some $^{13}C$ and/or $^{15}N$ amino acids are commercially available, albeit only in small quantities and only on occasion, most are not.

Recently, Fesik and coworkers have described a method for the production of isotopically labeled proteins from mammalian cells for NMR structural studies. (Biochemistry, 31, no 51, 12713, (1992)) These workers hydrolyzed both isotopically labeled algal and bacterial proteins with methanesulfonic acid in the presence of tryptamine and imidazole. The purpose of the latter reagents was to serve as "suicide bases" to reduce the destruction of the amino acids tryptophan and histidine respectively. The hydrolysate was then purified by the procedure described by LeMaster and coworkers; namely, by loading the hydrolysate onto a cation exchange column in the H+ form and eluting the amino acids, as a group, from the column with piperidine. The amino acid-containing fractions were combined, evaporated to dryness, redissolved in water, the pH adjusted to 11.5 with sodium hydroxide, and the resulting solution evaporated until the pH remained constant, "indicating that no more ammonia or piperidine was being removed." The amino acids were then filtered through a 500 molecular weight cutoff membrane to remove further impurities and lyophilized. The authors do not indicate whether the resulting amino acids were used directly (i.e. at high pH) or whether the pH of the solution was neutralized, and if so, with which acid. The Fesik et al. work, while representing a technological advance, nevertheless fails to provide a means for universally labeling mammalian cell expressed proteins useful for unambiguous NMR structural determinations. Firstly, the hydrolysis conditions employed destroy asparagine, glutamine and cysteine residues and leave just a "trace" of tryptophan (page 12715, Table 1). Secondly, the procedure employs piperidine as the eluant which is, as noted above, a toxic and controlled substance. Thirdly, LeMaster reports in his original paper that one of the "suicide bases," imidazole co-elutes with the amino acid leucine. LeMaster was able to remove the imidazole by crystallization of leucine. Fesik et al. do not describe such a crystallization step, and indeed, such a step would be impossible in the Fesik et al. procedure where the individual amino acids are not resolved.

Fesik et al. describe the removal of the piperidine eluant by raising the pH of the solution to 11.5 and heat evaporating the solution until the pH remained constant. At this pH, and particularly at the elevated temperatures necessary to remove piperidine (boiling point 106° C.), there is a risk of racemization and/or nucleophilic attack of the amino acids by the piperidine/sodium hydroxide mixture. Such reactions will reduce the amounts of viable amino acids in the mixture, reducing its efficiency as a growth medium. Moreover, as the authors themselves acknowledge, the heat evaporation step is stopped when a stable solution pH indicates "that no more ammonia or piperidine was being removed." It is therefore possible that the mixture of amino acids obtained will contain trace amounts of piperidine, a highly toxic material.

Of more significance however, are the absence of the amino acids asparagine, glutamine and cysteine and the presence of just a "trace" of tryptophan (page 12715, Table 1). Although the lack of asparagine residues was found to be unimportant in the systems investigated by Fesik et al., glutamine was found to be vital for cell growth (page 12716, FIG. 2). The authors provide a method of enzymatically synthesizing glutamine from glutamic acid as a supplement. However, for this reaction to be of value, a source of appropriately labeled glutamic acid has to be available. As the authors note, $^{13}$C, $^{15}$N labeled glutamic acid is commercially available. However, $^2$H-labeled glutamic acid, for instance, is not. There is great interest in obtaining $^2$H-labeled proteins for ligand/receptor studies (see below).

By contrast, Fesik provides no method for the preparation of labeled cysteine. Cysteine labeled with a stable isotope has been commercially available only in $^{15}$N-labeled form. Consequently, the approach adopted by Fesik and coworkers will not lead to universally labeled products in any case, except for simple $^{15}$N-labeling, as the cysteine and tryptophan residues will not be appropriately labeled. It is possible, moreover, that isotopic leakage of undesired isotope will occur from the incorrectly labeled cysteine residues into other amino acid residues by cellular metabolism.

Similarly, the "trace" amounts of tryptophan present in the mixture were insufficient for cell growth without supplementation (page 12715, Table 1; page 12716, FIGS. 1 and 2). Although $^{15}$N-labeled tryptophan is commercially available, neither $^{13}$C, $^{15}$N- nor $^2$H-labeled tryptophan is available. Thus for tryptophan to be introduced as a supplement for any labeling experiment other than for simple $^{15}$N-labeling will lead to the same problems associated with the absence of a suitable labeled cysteine residue, namely incomplete isotopic labeling.

Thus, the method provided by Fesik and coworkers will lead to the universal isotopic labeling of proteins only in the case of $^{15}$N-labeled proteins. Although the method is an advance, $^{15}$N-labeled amino acids are already available, as previously indicated. In the case of $^{13}$C, $^{15}$N-labeling experiments, cysteine and tryptophan residues will not be universally labeled, while in the case of $^2$H-labeling experiments, cysteine, tryptophan and glutamine residues will be incorrectly labeled.

There has also recently been published a paper by Hsu and Armitage (*Biochemistry*, 31 (51) 12778 (1992)) concerning the NMR determination of the structure of the immunosuppressant drug cyclosporin A bound to its receptor, cyclophilin. These workers labeled cyclophilin, expressed in bacteria, with the NMR inactive isotope $^2$H. They were thus able to examine the structure of the cyclosporin A/cyclophilin complex unencumbered with the signals from the cyclophilin. Given the importance of mammalian ligand/receptor interactions, there is thus also a requirement for mammalian cell proteins, particularly receptors, to be universally labeled with $^2$H. Heretofore, labeled mammalian nutrient media for accomplishing this goal have been unavailable.

Accordingly, for both structure-function studies in general and for rational drug design in particular, there is a need for universally labeled compositions and methods for determining the three-dimensional structures of mammalian cell proteins, and protein complexes. There is consequently a need for producing mammalian cell proteins labeled with a range of stable isotopes in universally labeled form.

SUMMARY OF THE INVENTION

In accordance with the present invention, a method for determining three-dimensional structural information of a protein involves the steps of (a) growing, under protein-producing conditions, a mammalian or insect cell culture which is capable of producing the protein of interest in a nutrient medium which contains all amino acids that are essential for growth of the cells and which contains assimilable sources of carbohydrate, essential minerals and growth factors, wherein the amino acids and any other substrate used by the cells for protein synthesis in such nutrient medium are substantially isotopically labeled with an NMR-active isotope; (b) isolating the labeled protein from the nutrient medium in substantially labeled form and (c) subjecting the protein to NMR spectroscopic analysis to determine information about its three-dimensional structure.

In another aspect of the invention, a method for determining three-dimensional structural information of a protein involves the steps of (a) growing, under protein-producing conditions, a mammalian cell culture which is capable of producing the protein of interest in a nutrient medium which contains all amino acids that are essential for growth of the cell line and which contains assimilable sources of carbohydrate, essential minerals and growth factors, wherein substantially all of the carbon atoms in the amino acids and the carbohydrate source in such nutrient medium are $^{113}$C; (b) isolating the labeled protein from the nutrient medium in substantially labeled form and (c) subjecting the protein to NMR spectroscopic analysis to determine information about its three-dimensional structure.

In yet another aspect of the invention, a method for determining three-dimensional structural information of a protein involves the steps of (a) growing, under protein-producing conditions, a mammalian or insect cell culture which is capable of producing the protein of interest in a nutrient medium which contains all amino acids that are essential for growth of the cell line and which contains assimilable sources of carbohydrate, essential minerals and growth factors, wherein substantially all of the carbon atoms in the amino acids and the carbohydrate source in such nutrient medium are $^{13}$C and substantially all of the nitrogen atoms in the amino acids in such nutrient medium are $^{15}$N; (b) isolating the labeled protein from the nutrient medium in substantially labeled form and (c) subjecting the protein to NMR spectroscopic analysis to determine information about its three dimensional structure.

In a further aspect, this invention is directed to the determination of three-dimensional structural information of a first molecule while complexed with a second molecule, wherein at least one of such molecules is a protein. The procedure involves substantially labeling the first molecule with a stable NMR-active isotope and substantially labeling the second molecule with deuterium, forming a complex between the first and second molecules and subjecting the complex to NMR spectroscopic analysis to determine information about the three-dimensional structure of the first molecule.

Another aspect of the invention involves a novel nutrient medium capable of supporting the growth of a mammalian or insect cell culture, which contains all amino acids that are essential for growth of the cells, an assimilable source of carbohydrate, and essential minerals and growth factors, wherein the amino acids and any other substrate used by the cells for protein synthesis are substantially labeled with $^{13}C$ or with both $^{13}C$ and $^{14}N$.

In still another embodiment, the invention involves a method for producing a mixture of amino acids in substantially completely isotopically labeled form, which comprises (a) growing a microbial culture in a nutrient medium in which substantially all of the carbon utilized as a substrate for protein biosynthesis is $^{13}C$; (b) recovering a protein fraction from the microbial culture; (c) hydrolyzing the protein under acidic, non-oxidizing conditions in the presence of a sulfhydryl reducing agent to produce a crude mixture of amino acids; (d) subjecting the crude mixture of amino acids to cation exchange chromatography to produce a partially purified mixture of amino acids; (e) subjecting the partially purified mixture of amino acids to anion exchange chromatography to produce a purified mixture of amino acids; and (f) supplementing the purified mixture of amino acids with an amount of $^{13}C$-labeled cysteine sufficient to support protein production by the mammalian or insect cells. The foregoing method may also be used to produce a mixture of $^{13}C$, $^{15}N$-doubly labeled amino acids or to produce a mixture of $^{2}H$-labeled amino acids.

DESCRIPTION OF THE INVENTION

This invention provides a means for determining three-dimensional structural information about mammalian or insect cell-produced proteins. Since mammalian and insect cells used as hosts for recombinant DNA are capable of producing complex proteins in a form similar or identical to their natural three-dimensional structure, this invention provides a valuable technique for studying the structure-function relationships of biologically active proteins. The procedure involves the growth of mammalian cell lines in a nutrient medium in which all of the amino acids are substantially completely labeled with one or more NMR-active isotopes. The invention allows for the universal labeling of proteins with $^{13}C$ or $^{15}N$ or both. The invention further provides for the universal labeling of proteins with $^{2}H$, so as to make them NMR invisible. The latter technique is particularly useful for obtaining structural information for molecules in complexes, such as, for example, hormone-receptor complexes. By making one of the binding partners NMR invisible, the structure of the other binding partner, when labeled with one or more NMR-active isotopes, can be studied.

The mammalian cell line nutrient media of this invention contain isotopically-labeled amino acids derived from microorganisms. Defined nutrient media for mammalian and insect cells are well-known. The growth requirements of these cells are well-understood, and synthetic media containing assimilable sources of carbohydrate, essential minerals and growth factors are commercially available. Some of these media further contain trace amounts of pyruvic acid. When media of this type are desired, it is advantageous to supply the pyruvic acid in appropriately labeled form. Isotopically labeled forms of pyruvic acid are commercially available. Serum-free defined media are commercially available. Serum-free media are preferred for practice of the present invention, so as to facilitate recovery of a relatively pure labeled protein for NMR analysis. Purification of the labeled protein from a serum-free mammalian or insect cell culture medium can be accomplished by any of a variety of known techniques. See, Deutscher, M. P., *Guide to Protein Purifications, Methods in Enzymology*, Vol. 182 (1990).

Universal labeling of proteins is accomplished by supplying all of the essential amino acids and any other substrates used by the cells for protein synthesis in labeled form. As used herein, protein synthesis includes the biosynthesis of carbohydrate side chains in the case of glycoproteins.

The invention provides a simple means of producing a mixture of amino acids. It is easy to perform, is non-hazardous to the user, and is readily scalable, which is important, given that large quantities of labeled media may be required to produce sufficient protein for NMR analysis.

The method of producing the labeled amino acid mixture relies on the fact that amino acids, as a class of compounds, can carry both a positive and a negative charge. They can thus be separated, as a group, both from neutral compounds and from compounds which can carry only a positive or only a negative charge, by absorption on, and elution from, acidic and basic ion exchange resins.

As used herein, an indication that a protein is "substantially labeled" or that "substantially all" of the atoms of a particular element in a molecule are in a given isotopic form means that the molecule is sufficiently enriched with the desired isotope that meaningful NMR spectral information can be obtained. In the case of NMR-active isotopes, such as $^{13}C$ and $^{15}N$, the degree of enrichment will be such that three-dimensional structural information can be deduced from the NMR spectra. In general, about 95% or more of the atoms of a given element will be in the desired isotopic form, preferably greater than about 98%.

In the case of $^{12}H$, the degree of enrichment will be such that the labeled molecule does not produce an NMR signal sufficient to interfere with an analysis of an NMR-active species complexed to it. In this case, the level of enrichment is greater than about 70%, with great than about 95% being particularly preferred.

Alternatively, the level of $^{2}H$ enrichment is such that the signals from the NMR-active nuclei, $^{11}H$, $^{13}C$ as $^{15}N$ are enhanced or better resolved. In general this level of enrichment will range from about 20% to about 70%.

The starting mixture of amino acids is a hydrolysate of a protein, labeled with the stable isotopes of choice. In accordance with the invention, the starting protein is substantially labeled with $^{13}C$, or with both $^{13}C$ and $^{15}N$ or with $^{12}H$. Many techniques have been published to produce such proteins, including growth of bacteria in the presence of labeled carbohydrate and salts (Kay, et al., supra), growth of bacteria in algal lysates (Chubb, R. T., et al., *Biochemistry*, 30, 7718 (1991)), growth of yeast in algal lysates (Powers, R., et al., *Biochemistry*, 31, 4334 (1992)), growth of bacteria and yeast in labeled methanol (See, Moat, A. G. and Foster, J. W., *Microbial Physiology*, 2d Ed., John Wiley & Sons, New York (1988), p. 218) and the phototropic culture of algae in the presence of isotopically labeled $^{13}CO_2$ and/or $^{15}N$ salts (Cox, J., et al., *Stable Isotopes in Pediatric Nutritional and Metabolic Research*, Chapman, T. E. et al., Eds., Intercept Ltd., Andover House, England (1950), p. 165). Similarly, many procedures for the hydrolysis of proteins have been published, including hydrolysis with hydrochloric acid, methanesulfonic acid (LeMaster, et al., supra) and enzyme hydrolysis. If an enzyme hydrolysis is used then it is convenient to acidify the hydrolysate. This has the advantage of denaturing and precipitating the enzyme, which can then be removed from the hydrolysate by centrifugation.

In the present method, acid hydrolysis is preferred. The acid hydrolysis is advantageously conducted using a strong mineral acid, such as hydrochloric acid, nitric acid or sulfuric acid or a sulfonic acid such as p-toluenesulfonic acid or methanesulfonic acid, the latter being preferred. The acid concentration may vary, depending upon the nature of the protein substrate, but in general is sufficient to effect complete hydrolysis. Typically, acid concentrations range from about 1N to about 6N, preferably from about 2N to about 4N. The acid hydrolysis is carried out under non-oxidizing conditions. These conditions can be achieved by conducting the reaction in vacuo or by purging with an inert gas such as nitrogen, argon or the like.

The protein to be hydrolyzed may be added to the hydrolysis medium at a concentration of between about 0.5 g/10 ml and 5 g/10 ml, preferably at a concentration of between about 1 g/10 ml and 2.3 g/10 ml.

The hydrolysis is conducted at a temperature and for a time sufficient to effect substantially complete hydrolysis, while minimizing racemization or the loss of labile amino acids. The temperature of the hydrolysis generally ranges from about 90° to 140° C., but in order to minimize the racemization of amino acids is preferably in the range 100° to 115° C., with 100° C. particularly preferred. The time of hydrolysis may be in the range of 24 to 72 hours, depending on the protein to be hydrolyzed. Preferably a hydrolysis time of about 48 h is used.

The amino acids that are susceptible to degradation by oxidation are further protected by the presence of a reducing agent. Preferably, a strong sulfhydryl-containing reducing agent is employed, such as thioglycollic acid (Fasman, G. D., Ed., *Practical Handbook of Biochemistry and Molecular Biology*, CRC, New York (1989), p. 106). The purpose of the reducing agent is not just to protect the vulnerable tryptophan and histidine residues but also the sulfhydryl-containing cysteine residues. If thioglycollic acid is used, it can easily be subsequently removed according to the procedure of the invention.

The reducing agent is employed at a concentration in the hydrolysis mixture sufficient to prevent substantial destruction of tryptophan, histidine and cysteine. For thioglycollic acid, such concentration generally ranges from about 1 to about 7% v/v, preferably from about 3 to about 5% v/v.

The hydrolysate is added to a column of a cation ion exchange resin. The cation exchange resin is preferably in an acid form. In principle, any acid form of resin may be used, but for convenience the resin is in the form of a simple acid such as $H^+$, pyridinium, methylammonium etc. Cation exchange resins that may be used in this method include, Dowex 50×8-400 available from Dow Chemical Co., Midland, Mich. After addition of the hydrolysate to the resin, neutral and acidic contaminants are removed by washing the resin with an acidic solution. In principle, any acid can be used, and for convenience a simple mineral acid such as hydrochloric, sulfuric acid, etc. may be used. The acidic solution has a pH below the pKa of the most acidic amino acid, but not so low as to cause substantial racemization. In general, the pH ranges from about 1 to about 2, preferably about 2. The volume of the acidic solution is sufficient to remove substantially all of the material and acidic contaminants. Elution with about 2-6 bed volumes is usually sufficient.

The acid solution is then removed from the resin by washing the resin column with water. To ensure removal of contaminants the volume of water used is preferably in the range of 2-6 bed volumes.

Following removal of the acid wash with water, the amino acids and the basic materials adhering to the cation exchange resin are eluted with a basic solution. In principle, any basic solution can be used, and advantageously, a simple base such as sodium hydroxide, potassium hydroxide, or a nitrogenous base with the general formula $NR^1R^2R^3$, where $R^1$, $R^2$, and $R^3$ are each independently hydrogen, or $C_1-C_4$ alkyl or alkenyl groups, may be used. Examples of such nitrogenous bases include aqueous ammonia, aqueous methylamine, aqueous triethylamine, etc. The basic medium neutralizes the acidic cation exchange resin with concomitant elution of the bound amino acids and basic compounds. The pH of the basic medium is such that the amino groups of the amino acids are neutral while the carboxylate functions of the amino acids are negatively charged. The pH of the basic medium preferably is greater than about 10. To avoid racemization of the amino acids under too strongly basic conditions, the pH advantageously is less than about 13 and preferably is in the range of about 10–11. The basic medium neutralizes the acidic cation exchange resin with concomitant elution of the bound amino acids and basic compounds.

The amino acid mixture may be further purified by anion exchange chromatography. The eluate from the cation exchange column is added to a column of anion exchange resin in a basic form. In principle, any basic form of the resin can be employed, and preferably a simple basic form such as hydroxide is used. Suitable anion exchange resins include Dowex 1×8-100, available from Dow Chemical Co., Midland, Mich. The amino acids are absorbed onto the basic ion exchange resin because, while their amino groups now carry no positive charge, their carboxyl functions are now negatively charged.

The basic and neutral contaminants are removed by washing the resin with a basic solution. The basic solution used in this step may be any of the basic solutions described from the elution of the amino acids from the cation exchange column.

The basic medium is removed from the anion exchange column by elution with water. It is preferred that no basic medium is left in contact with the amino acids bound to the resin, and therefore, about 2-8 bed volumes, preferably at least about 4 bed volumes, of water are used to wash the column.

The amino acids are eluted from the basic anion exchange resin with acid. In principle, any acid solution may be used but for preference, a solution of weak, volatile acid that may be removed by subsequent evaporation is used. Either formic or acetic acid are therefore preferred. The concentration of acid used is such that the pH of the acidic solution is in the range of about 2–6, preferably in the range of about 3–5. The purified amino acids are thus eluted from the column as an off white solution. A further advantage of the invention is that aspartic acid is eluted after all the other amino acids. For instance, all the amino acids except aspartic acid may be eluted from the column with 0.25% v/v aqueous acetic acid. Aspartic acid may then be eluted from the column with 2.5% v/v aqueous acetic acid. A further aspect of the invention is therefore a simple purification of the amino acid aspartic acid.

It will be appreciated by those skilled in the art that the above elution procedure is a so-called "step-gradient" elution. It will further be appreciated that a linear, or alternatively an exponential, gradient of concentration of the eluting acid may be used. Such gradients will lead to sequential elution of the amino acids, either as mixtures or as single amino acids depending on the gradient used. A further aspect of the invention is therefore a simple procedure for the purification of amino acids, either singly or as mixtures. Another aspect of the invention is that the amino acids thus isolated may be used to alter the amino acid profile of the overall amino acid mixture. Yet another aspect of the invention is that the overall amino acid mixture can thus be tailored to the requirements of a given cell line.

The isolated amino acids may now be isolated by a standard technique such as evaporation under reduced pressure, or lyophilization. A further aspect of the invention is that the amino acids will be isolated in substantially pure form because the acid eluant used is highly volatile.

A further advantage of the invention relates to the fact that one amino acid, arginine, is much more basic than all the others. It will therefore be eluted last from the cation exchange column, after the other amino acids and after all the contaminants. On elution at a pH in the range of 10–12, arginine will carry no charge. This is due to the presence of its highly basic guanidinium side chain which will carry a positive charge at pHs in the range 10–12 and which will neutralize the negative charge of the carboxylate function. Unlike all the other amino acids therefore, arginine will pass through the cation exchange resin, after all the contaminants, and can be subsequently isolated and crystallized, for instance as the hydrochloride, by standard techniques (Cox, G. J., *J. Biol. Chem.*, 78, 475 (1928)). A further aspect of the invention is therefore a simple purification of the amino acid arginine.

It will be appreciated by those skilled in the art that the invention, particularly if a sulfhydryl containing reducing agent was used for the hydrolysis step, leads to a mixture of pure amino acids in the same proportion as was in the starting hydrolysate, with little or no variation in yield of each amino acid. A further aspect of the invention is therefore a means of simply preparing a mixture of pure amino acids in the same proportions as in the starting protein. The proportions of the amino acids can therefore be controlled by selecting the appropriate starting protein or mixture of proteins. Alternatively, the mixture of amino acids prepared according to the invention may be supplemented by the addition of an amino acid or acids that are available either commercially or which can be synthesized.

For example, cysteine is an important amino acid in mammalian cell media, yet is not present in high enough concentrations in most bacterial, yeast or algal proteins to support mammalian protein biosynthesis in mammalian on insect cells.

Enzymatic procedures for the synthesis of cysteine are known. For example, U.S. Pat. No. 4,733,011 to Miyahara et al., incorporated herein by reference, discloses a method for preparing L-cysteine from L-serine by enzymatic reaction with hydrogen sulfide. U.S. Pat. No. 4,782,021 to Ishiwata et al., incorporated herein by reference, describes the production of L-serine by reacting lysine and formaldehyde in the presence of serine hydroxymethyltransferase. Isotopically labeled cysteine, including $^{13}$C-cysteine, $^{13}$C, $^{15}$N-cysteine and perdeuterated cysteine may be prepared by those procedures using commercially available substrates.

It will be appreciated by those skilled in the art that mammalian cell media contain, in addition to amino acids and glucose, various compounds such as vitamins, fatty acids, essential minerals and growth factors. A further aspect of the invention is that the mixture of pure labeled amino acids produced by the invention may be added to any mixture of growth factors tailored for a given cell line, thereby producing an isotopically labeled medium for any mammalian or insect cell line. In addition to isotopically labeled amino acids, other substrates utilized by the cells for protein synthesis may be provided in labeled form. For example, carbohydrate, such as glucose, can be provided in the $^{13}$C-labeled form or in deuterated form.

It will be further appreciated by those skilled in the art that conventional protein hydrolysis procedures destroy the amino acids arginine and glutamine, with concomitant formation of the acidic amino acids aspartic and glutamic acid respectively. Most mammalian cell media contain large quantities of glutamine. Unexpectedly, addition of glutamine to the mixture of amino acids produced by this invention produced no increase in the either the growth rate of mammalian cells or productivity of recombinant protein grown on a mixture of amino acids produced by this invention. A further aspect of the invention is that the mixture of amino acids produced by the invention does not need supplementation with glutamine to support mammalian cell growth. It has been found that when the preferred conditions described here are used, no detectable racemization occurs.

A further aspect of the invention is that amino acids of any isotopic substitution can be purified by the process of the invention. Because the invention relies on the protonation of the amino and carboxylic functions of the amino acids only, amino acid mixtures of any isotopic labeling can be purified by the invention.

Whatever the isotopic labeling, the resulting mixture of amino acids is sufficient to support the growth of mammalian or insect cells. Yet another aspect of the invention is that the resulting mammalian or insect cells and their metabolic products will be universally labeled with the same isotopic mixture as the starting material.

The invention is illustrated by the following examples, which are included by way of illustration only and in no way restrict the scope of the invention.

EXAMPLES

Example 1

An algal biomass (500 g) from a culture of Chorela sp was diluted (H₂O) to approx 10% slurry, placed in ice, and the cells broken by three passages through a Microfluidizer. The resulting slurry was centrifuged at 5,000 rpm for 15 mins. at 5° C. The supernatant was collected, and the pellet resuspended in H₂O and recentrifuged under the same conditions. This process was repeated twice. The supernatants were combined, treated with trichloracetic acid (final concentration 5% v/v) and the whole stored at 5° C. overnight.

The resulting suspension was centrifuged at 5,000 rpm at 5° C. for 30 mins. The supernatant was decanted, the pellet resuspended in an equal volume of acetone, and the whole centrifuged at 5,000 rpm at 5° C. for 15 mins. The supernatant was removed, the pellet suspended in 500 ml of ethanol/ether and collected by filtration under reduced pressure. The pellet was washed with ethanol/ether and dried under reduced pressure.

Seven grams of a soluble protein fraction described above was heated in vacuo in 3M methanesulfonic acid (70 ml) containing 4% v/v thioglycollate for 48 h at 100° C. On cooling, the hydrolysate was slowly poured onto water (70 ml) cooled in an ice bath and the resulting mixture left to stand for approx. 10 min. The resulting cooled solution was centrifuged (RC-3B, 250 ml bucket, 5,000 rpm, 10 min.). The supernatant was pumped (36 ml/min.) onto a column of Dowex 50×8 ion exchange resin (H+ form, 500 g) equipped with an FMI Lab Pump QSY at its base.

When all the hydrolysate had been pumped onto the column, dilute aqueous $H_2SO_4$ (pH2.0, 1.5 L) followed by $H_2O$ (2 L) were pumped (36 ml/min.) throughout the column. Fractions (labeled H+,500 ml) were collected from the bottom of the column.

The H+ column was then connected via the pump to a column of Dowex 1×8-100 ion exchange resin (OH-form, 500 g). Dilute aqueous ammonia (1%v/v, 9 L) was pumped (36 ml/min.) through the H+ column and the effluent carried throughout to the OH− column. Fractions (labeled OH−, 500 ml) were now collected from the base of the OH− column.

TLC analysis (Analtech Silica GS plates, n-BuOH:AcOH:H₂O (2:1:1 v/v)), developer:ninhydrin (1% v/v in MeOH:Glac AcOH (97:3 v/v)) revealed the presence of arginine in fractions OH-13-18.

After elution of the arginine fractions, the pump was stopped and connected directly to the OH− column. The pump was restarted while fractions (500 ml) continued to be collected from the OH− column.

Dilute aqueous acetic acid (0.25% v/v, 10 L) was then pumped through the OH− column while 500 ml fractions continued to be collected from the base of the column. Pumping continued until no further ninhydrin-positive spots were detected in the effluent.

TLC analysis (Analtech Silica GS plates, n-BuOH:AcOH:H₂O (2:1:1 v/v)), developer:ninhydrin (1% v/v in MeOH:Glac AcOH (97:3 v/v)) revealed the presence of mixed amino acids (fractions OH-25-36).

The arginine containing fractions and the mixed amino acid fractions were independently dried and concentrated by freeze drying. The residues were dissolved in water, filtered through 0.22 micron filters into sterile bottles and re-freeze dried. The arginine fraction was crystallized as the hydrochloride essentially according to the procedure described in Cox, J., supra, yield 0.31 g. The mixed amino acid fractions were isolated as a pale yellow powder, yield 4.6 g.

Example 2

CHO-SSFM-1 media (Gibco), a serum-free medium optimized for CHO cells, was obtained from the suppliers with the amino acids omitted. Two media samples were prepared as follows:

To 200 ml of amino-acids-free CHO-SSFM-1 aliquots were added
1. Mixed amino acids (340 mg)+cysteine(20 mg)+crystallized arginine(40 mg)
2. Mixed amino acids (340 mg)+cysteine(20 mg)+crystallized arginine(40 mg)+glutamine(120 mg).

The solutions were sterilized by passage through 0.22 micron filters and aliquots (2–3 ml) were inoculated with CHO cells (initial concentration $1 \times 10^5$/ml). Cell counts and % viable cells (%) were recorded relative to a sample of control CHO-SSFM-1 media.

|  | 48 h | 72 h | 96 h | 120 h | 144 h | 168 h |
| --- | --- | --- | --- | --- | --- | --- |
| Control | 2.4 (99) | 5.2 (96) | 7.0 (93) | 7.0 (91) | 5.6 (83) | 4.0 (64) |
| 1 | 1.6 (99) | 3.8 (93) | 5.1 (97) | 12.0 (92) | 8.2 (84) | 5.0 (72) |
| 2 | 2.2 (99) | 4.0 (95) | 5.5 (93) | 7.2 (95) | 7.2 (82) | 7.0 (69) |

These results indicate that i) that the amino acid mixture obtained by the method of this Example gave growth characteristics indistinguishable from that of the control and ii) that the addition of glutamine was not necessary for cell growth.

I claim:

1. A nutrient medium capable of supporting the growth of a mammalian or insect cell culture, which contains all amino acids that are essential for growth of the cells, an assimilable source of carbohydrate, and essential minerals and growth factors, wherein the amino acids and any other substrate used by the cells for protein synthesis are substantially labeled with both $^{13}C$ and $^{15}N$.

2. The nutrient medium of claim 1, wherein carbohydrate source is substantially labeled with $^{13}C$.

* * * * *

UNITED STATES PATENT AND TRADEMARK OFFICE
CERTIFICATE OF CORRECTION

PATENT NO. : 5,393,669

DATED : February 28, 1995

INVENTOR(S) : Jonathan M. Brown

It is certified that error appears in the above-indentified patent and that said Letters Patent is hereby corrected as shown below:

Col. 2, line 49, after "containing" insert -- $^{13}C$ --; Col. 6, line 49, "$^{113}C$" should be -- $^{13}C$ --; Col. 8, line 61, "$^{11}H$" should be -- $^{1}H$ --; Col. 8, line 68, "$^{12}H$" should be -- $^{2}H$ --; Col. 12, line 45, delete "the" (first occurrence); Col. 14, line 41, delete "that" (first occurrence).

Column 8, line 54, "$^{12}H$" should be -- $^{2}H$ --.

Signed and Sealed this

Twenty-seventh Day of June, 1995

Attest:

BRUCE LEHMAN

*Attesting Officer*   *Commissioner of Patents and Trademarks*